United States Patent [19]
Kerkhoff et al.

[11] Patent Number: 5,237,181
[45] Date of Patent: Aug. 17, 1993

[54] METHOD OF INSPECTING A WEB OF TRANSLUCENT MATERIAL, ESPECIALLY PHOTOGRAPHIC PAPER

[75] Inventors: Alois B. Kerkhoff; Wolfgang Storbeck, both of Bissendorf, Fed. Rep. of Germany

[73] Assignee: Felix Schoeller jr GmbH & Co. KG, Osnabrueck, Fed. Rep. of Germany

[21] Appl. No.: 804,152

[22] Filed: Dec. 6, 1991

[30] Foreign Application Priority Data

Dec. 8, 1990 [DE] Fed. Rep. of Germany ....... 4039196

[51] Int. Cl.⁵ .............................................. G01N 21/86
[52] U.S. Cl. ..................................... 250/571; 356/429
[58] Field of Search ................ 358/101, 106; 250/571, 250/572, 559, 563; 356/388, 390, 392, 394, 429, 430, 431

[56] References Cited

U.S. PATENT DOCUMENTS

| | | |
|---|---|---|
| 2,648,723 | 8/1953 | Goldsmith . |
| 4,590,511 | 5/1986 | Bocchi et al. ........................ 358/101 |
| 4,644,174 | 2/1987 | Ouellette et al. .................... 250/559 |
| 4,760,271 | 7/1988 | Brenholdt ............................ 250/559 |
| 4,857,747 | 8/1989 | Bolton et al. ........................ 250/563 |
| 4,872,024 | 10/1989 | Nagai et al. ......................... 358/101 |
| 4,918,522 | 4/1990 | Pajunen ............................... 358/106 |
| 4,931,657 | 6/1990 | Houston et al. ..................... 250/559 |
| 4,954,883 | 9/1990 | Belmares-Sarabis et al. ....... 358/106 |
| 4,991,007 | 2/1991 | Corley ................................. 358/106 |
| 5,113,454 | 5/1992 | Marcantonio et al. ............. 358/106 |
| 5,128,753 | 7/1992 | Lemelson ............................ 358/101 |

Primary Examiner—David C. Nelms
Attorney, Agent, or Firm—Sprung Horn Kramer & Woods

[57] ABSTRACT

A method of visually inspecting the formation of a web of translucent material by means of a device it moves past. The device consists of a source of light on one side of the web generating a beam of light of a desired hue and intensity that penetrates the web, and a video camera on the side of the web away from the source of light, intercepting the beam and converting it into a video signal that is forwarded to a monitor. The source of light emits the beam in a flash of duration $t_1$ that is too short for the web to advance far enough while illuminated to blur the image. The image on the monitor is accompanied by a reference image.

13 Claims, 1 Drawing Sheet

METHOD OF INSPECTING A WEB OF TRANSLUCENT MATERIAL, ESPECIALLY PHOTOGRAPHIC PAPER

BACKGROUND OF THE INVENTION

The present invention concerns a method of visually inspecting the "formation" of a web of translucent material, especially photographic paper by means of a device it moves past, consisting of (1) a source of light on one side of the web, generating a beam of light of a desired hue and intensity that penetrates the web, and (2) a video camera on the side of the web away from the source of light, intercepting the beam and converting it into a video signal that is forwarded to a monitor. The signal can be forwarded directly, by way of a digital (pixel) memory, or both.

Such a method is known from the U.S. Pat. No. 4,857,747, which describes a method and device for the on-line inspection of a web of material to determine what is called its "formation". The device operates with a source of light positioned across the web and with a "CCD" (charge-coupled device) camera that intercepts a signal capable of being digitized. Appropriate circuits standardize and test the digitized signal, pixel by pixel, and generate a "formation index" for the total width of the web.

The known method demands extensive computer and memory capacity. It is, however, still difficult, in spite of the expenditure, to obtain a signal-to-noise ratio powerful enough for reliable results. Paper in particular is a natural product with properties, which should be classified under the overall term "formation," that reveal themselves to one of skill in the art peering through the web. It is, however, extremely difficult to obtain indices just from the information that can be derived from the individual pixels.

The scanning rate at the present state of the art is limited by the limited rates of the optical and data-processing equipment. The monitoring system monitors the overall width of the web in one instant with a 2048 pixel/line camera. The scanning rate is about 5000 per second, which corresponds to an illumination lasting 200 $\mu$sec per scan. For a web traveling at 10 m/sec, this corresponds to an advance of 2 mm. In paper and cardboard this can lead to considerable blurring, which can, in turn, lead in particular to erroneous evaluation of the mottle in photographic papers.

The method described in the aforesaid U.S. patent is accordingly appropriate only for "normal" paper, meaning paper with an area weight of 50 to 120 g/m$^2$. With this method the illumination lasts too long for inspecting the structure of semi-cardboards (with an area weight of 120–190 g/m$^2$) and cardboards (with an area weight of 190–300 g/m$^2$), and results in blurring.

Semi-cardboards and cardboards, however, have a relatively uniform formation that make it difficult to detect deviations from the norm. The differences in fiber distribution are accordingly more difficult to evaluate. In photographic papers in particular there is a relationship between fiber distribution and mottle in the developed photograph. Mottle is caused by variations in the optical density of the picture. This undesirable phenomenon is provoked by the surface of the underlying paper. Irregular surfaces will produce an apparent creep in even a perfectly smoothly applied emulsion, which will show up in the developed photograph as mottle, i.e. fluctuations in optical density. A paper's irregularity depends extensively on the fibrous structure of the pulp and on the occurrence of flocculation while the sheet is forming. The effect will appear even when the paper has been super-calendered and even coated.

These phenomena cannot be tested for with the known method of inspection.

Paper formation is usually determined by peering through the web. This approach has the drawback of being somewhat subjective, although it has been demonstrated that the human eye and human experience always lead to better results in analyzing paper formation and discovering defects than do computer programs, no matter how clever (Cresson, T.M., Tomimasu, H., and Lumer, P., "Characterization of Paper Formation", *TAPPI Journal*, Jul. 1990, pp. 153 ff.).

SUMMARY OF THE INVENTION

The principal object of the present invention is to improve a device of the aforesaid type to the extent that it will allow analysis of the formation of a web of paper etc. accurate enough to comply with the requirements of the photographic, textile, and printing industries and as commensurate as possible with the physical and psychological capacities of a human observer without inducing fatigue.

This object, as well as other objects that will become apparent from the discussion that follows, are achieved in accordance with the invention in a particularly advantageous method of inspecting a web of translucent material, especially paper, semi-cardboard, and cardboard, that will be employed as a support for a photographic emulsion. This method is characterized, in accordance with the invention, in that the source of light always emits the beam in a flash of duration $t_1$ that is too short for the web to advance far enough while illuminated to blur the image, and in that the image on the video monitor is always accompanied by a reference image.

Essential to the method is a camera with a flash lamp. The lamp is positioned above the web and the camera below it. This arrangement is of course not imperative. The lamp could be on the bottom and the camera on top or, in the event of an upright web, they could be on opposite sides. The camera and lamp will preferably be capable of moving parallel with the web, with an arbitrarily selected section of the web at a time being imaged, more or less on the order of 5=5 to 20=20 cm or even larger.

The ratio of web speed to duration of illumination must ensure negligible blurring, with a web advance of 0.5 mm or less for a duration $t_1$ having been demonstrated acceptable. The flash should last less than 100 and preferably between 10 and 40 $\mu$sec.

The result is a freeze frame of a particular section of web, preferably obtained by a CCD camera and already having a pixel matrix that will be easy to digitize. The camera forwards the signal containing the image to a monitor. This empirical image is accompanied by a reference image. The empirical image can be displayed on one monitor and the reference image on an adjacent monitor, or they can be displayed in adjacent sections on the same monitor. It is also possible to superimpose one image on the other to facilitate comparison when desirable. All of these modes of display are to be designated "visually associable." The reference image is obtained from a sample (paper, semi-cardboard, or cardboard) with a satisfactory formation. Comparing freeze frames will facilitate reliable evaluation of the paper's or cardboard's qualities because they exhibit extremely slight blurring, slight enough for the orientation and distribution of fibers to be very precisely perceptible. The method can accordingly be continuously employed for a wide range of area weights, from 50 to 300 g/m$^2$.

The intervals between exposures will be long enough to allow the inspector to view the adjacent images comfortably, one every 60 seconds for example.

The camera lens can have filters—polarizing, color, and/or gray filters, for example—and other optical devices mounted over it are well known in the art. CCD cameras are commercially available and do not in themselves constitute part of the invention. A regular videcon camera of the type used to generate video signals can be employed instead of a CCD camera. The only criteria are adequate resolution and light sensitivity for a usable image.

It is also essential for the video image to be forwarded not only directly to the monitor but also through a data processor which will digitize its colors and/or gray levels, modifying if necessary its digitized signal content and forwarding the modified form to the monitor. It will accordingly be possible to generate false-color images, for example, to emphasize specific characteristics and facilitate visual analysis. The data processor will preferably also accommodate digital-image memories, allowing a previously generated image to be displayed.

The preferred embodiment of the invention will now be described with reference to the drawing.

BRIEF DESCRIPTION OF THE DRAWING

The sole figure schematically illustrates in detail a device in accordance with the invention.

DESCRIPTION OF THE PREFERRED EMBODIMENT

Figure 1:
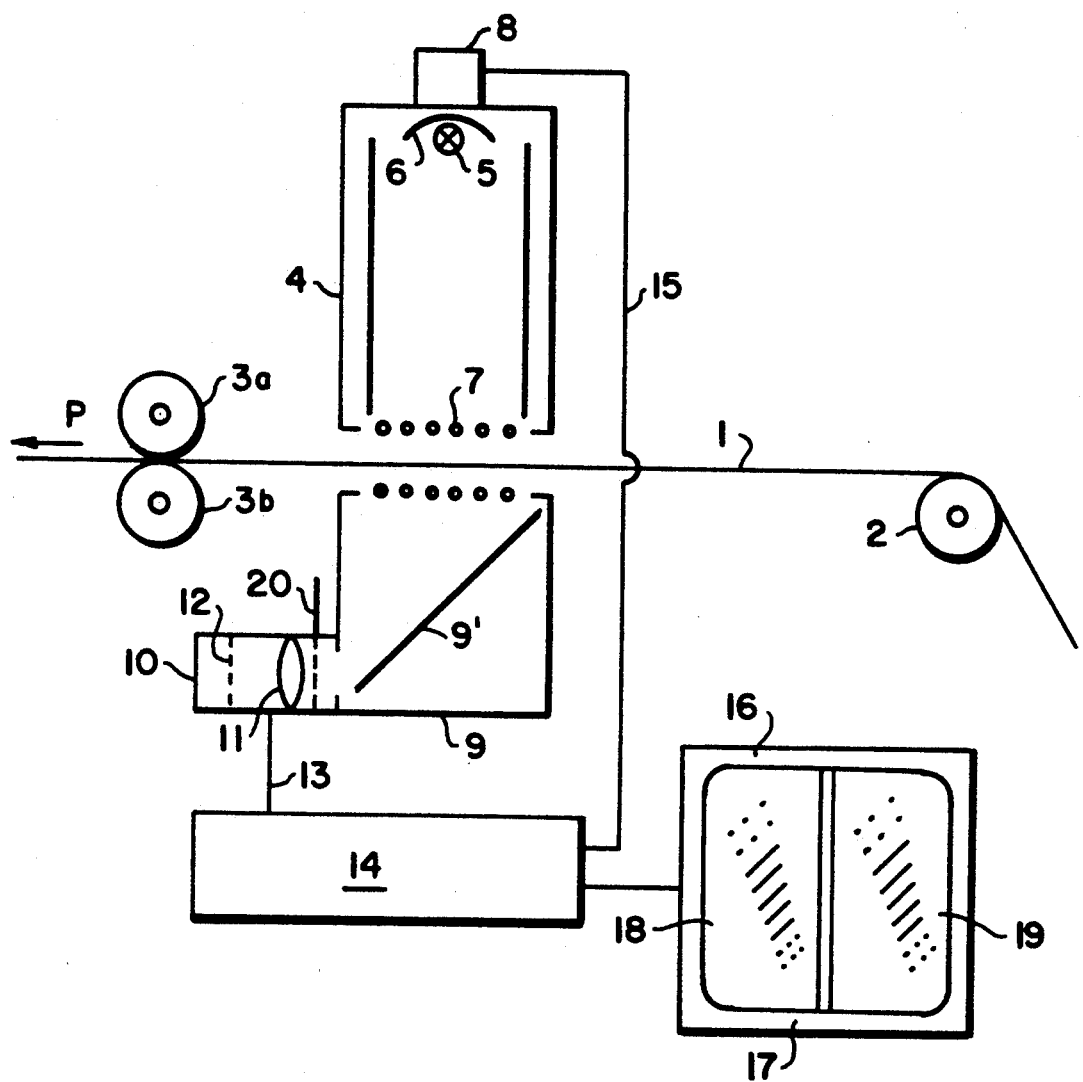

A device for carrying out the method in accordance with the invention is positioned in the vicinity of a web 1 of paper. The web travels over deflection and driving cylinders 2 and 3a and 3b in the direction indicated by the arrow P and at a rate of 2 to 10 m/sec. The paper has an area weight of 70 to 250 g/m$^2$.

Reflector shafts 4 are positioned about 1 cm above web 1. At the top of each shaft, a flashing xenon lamp 5 is mounted in front of a reflector 6 that concentrates its light into a high-energy parallel beam. A milk-glass diffusor 7 diffuses the beam, which then travels through the web. Other flash lamps can be in the form for example of LED's, laser diodes, or special sources of pulsed light.

The color and intensity of the light shining on the web can be varied. The period during which the flash lamps are on can be synchronized with a camera. The lamps, only one of which is illustrated, can also be wired to flash stroboscopically or cascaded.

On the other side of the web 1—i.e., below it in this embodiment—is a light-deflecting device in the form of a box 9 accommodating a mirror that reflects the incoming light through the lens 11 of a camera 10 and onto a light-sensitive CCD matrix 12. Camera 10 is accordingly positioned in front of the box 9, where it can easily be accessed. Filters 20—polarizing filters, for example—can be positioned upstream of camera 10.

CCD matrix 12 generates by a known process a video signal that is conveyed to a data processor 14 over a line 13. The processor digitizes the signal in relation to hue and/or gray levels or other characteristics. The data processor 14 also incorporates electronic filter circuits that can be employed to shape the signal. It can also have electronic memories that can store and release the digitized signal at any time. Such procedures are known in video processing and need not be described in detail herein.

The camera 10 has a vertically and horizontally resolving pixel matrix with a horizontal resolution, for example, of 378 pixels and a vertical resolution of 485 in what is called a 2:1 interlaced mode.

Each flash lasts less than 100 $\mu$sec and preferably 10 to 40 $\mu$sec, allowing exposures at a continuous web speed of approximately 5 to 10 m/sec without any essential blurring of the image because the web will advance less than 0.5 mm over the duration of a flash.

The flash is activated over a line 15 and by way of charging and discharging devices 8. The video signal, processed if necessary, is supplied to a monitor 16 with a screen 17 by conventional linear scanning. In the present case, the empirical image 18 is placed on the left half of the screen and the reference image 19 on the right half. The inspector can accordingly view the two adjacent images simultaneously. The two images will remain displayed until the inspector has sufficient information and can store them if desired on a tape recorder by an audible command. Another area of the web will now be imaged either automatically or on command. It has been demonstrated that this type of analysis supplies more useful results than does the scanning method at the state of the art. The interval between exposures is more or less one to five minutes. The device can travel across the web and focus on an arbitrarily selected section. Although the device has been primarily conceived for webs of paper and cardboard, it can also be employed for fabrics with fine patterns.

There has thus been shown and described a novel method of visually inspecting the formation of a web of translucent material, especially photographic paper, that fulfills all the objects and advantages sought therefor. Many changes, modifications, variations, and other uses and applications of the subject invention will, however, become apparent to those skilled in the art after considering this specification and the accompanying drawing, which disclose the preferred embodiment thereof. All such changes, modifications, variations, and other uses and applications that do not depart from the spirit and scope of the invention are deemed to be covered by the invention, which is to be limited only by the claims that follow.

What is claimed is:

1. In a method of visually inspecting the formation of a web of a translucent material selected from the group consisting of paper and cardboard by means of a device it moves past, consisting of (1) a source of light on one side of the web, generating a beam of light of a desired hue and intensity that penetrates the web, and (2) a video camera on the side of the web away from the source of light, intercepting the beam and converting it into a video signal that is forwarded to a monitor, the improvement wherein the source of light emits the beam in a flash of duration $t_1$ that is sufficiently short for the web to advance a maximum distance of 0.5 mm while illuminated to to avoid blurring the image, and wherein the image on the monitor is accompanied by a reference image.

2. The method defined in claim 1, wherein the duration $t_1$ lasts less than 100 μsec.

3. The method defined in claim 2, wherein the duration is in the range of 10 to 40 μsec.

4. The method defined in claim 1, wherein the web advances at a speed in the range of 5 to 15 m/sec.

5. The method defined in claim 1, wherein the reference image and the image generated by the camera are displayed in adjacent relationship on a single monitor.

6. The method defined in claim 1, wherein the video signal from the camera is supplied to a data processor for digitization with respect to at least one of hue and gray levels.

7. The method defined in claim 6, wherein the data processor modifies the digitized signals by electronic filters and displays the signals as modified on the monitor.

8. The method as in claim 1, wherein an arbitrarily selected section of the web is focused on by the camera.

9. The method defined in claim 1, wherein an arbitrarily selected section of the web is illuminated by the source of light.

10. The method defined in claim 8, wherein the camera can be displaced in relation to the web.

11. The method defined in claim 9, wherein the source of light can be displaced in relation to the web.

12. The method defined in claim 1, further comprising at least one polarization filter arranged between the source of light and the camera.

13. The method defined in claim 1, further comprising at least one color filter arranged between the source of light and the camera.

* * * * *